United States Patent
Hashizume et al.

(10) Patent No.: US 12,313,579 B2
(45) Date of Patent: May 27, 2025

(54) ODOR SENSOR, ODOR MEASUREMENT SYSTEM, AND METHOD FOR PRODUCING ODOR SENSOR

(71) Applicant: AROMA BIT, Inc., Tokyo (JP)

(72) Inventors: Kenichi Hashizume, Tokyo (JP); Masahiro Kishida, Fukuoka (JP); Erika Terada, Tokyo (JP); Kenichi Maeno, Tokyo (JP)

(73) Assignee: AROMA BIT, INC., Tokyo (JP)

( * ) Notice: Subject to any disclaimer, the term of this patent is extended or adjusted under 35 U.S.C. 154(b) by 313 days.

(21) Appl. No.: 17/789,482

(22) PCT Filed: Dec. 25, 2020

(86) PCT No.: PCT/JP2020/048945
§ 371 (c)(1),
(2) Date: Jun. 27, 2022

(87) PCT Pub. No.: WO2021/132639
PCT Pub. Date: Jul. 1, 2021

(65) Prior Publication Data
US 2023/0031936 A1 Feb. 2, 2023

(30) Foreign Application Priority Data
Dec. 27, 2019 (JP) .................. 2019-237839

(51) Int. Cl.
*G01N 27/12* (2006.01)
*G01N 5/02* (2006.01)
*G01N 33/00* (2006.01)

(52) U.S. Cl.
CPC .......... *G01N 27/125* (2013.01); *G01N 5/02* (2013.01); *G01N 33/0027* (2013.01);
(Continued)

(58) Field of Classification Search
CPC ......... G01N 27/12; G01N 27/126–128; G01N 33/0027; G01N 33/0031; G01N 2291/0215
See application file for complete search history.

(56) References Cited

U.S. PATENT DOCUMENTS

2018/0003604 A1* 1/2018 Shiba .................. G01G 3/13
2018/0266977 A1* 9/2018 Hashizume .......... G01N 27/227

FOREIGN PATENT DOCUMENTS

CN  106324046 A  1/2017
JP  H05-187986 A  7/1993
(Continued)

OTHER PUBLICATIONS

Written Opinion for PCT/JP2020/048945; mailed on Apr. 6, 2021.
(Continued)

*Primary Examiner* — Nathaniel J Kolb
(74) *Attorney, Agent, or Firm* — Fresh IP PLC; Clifford D. Hyra; Aubrey Y. Chen

(57) ABSTRACT

To provide an odor sensor capable of using an additive that was not capable of being adopted in an odor sensor including a polymer film, an odor measurement system using the odor sensor, and a method for producing the odor sensor, an odor sensor comprises a plurality of sensor elements, the sensor element including a substance absorption film adsorbing an odor substance; and a detection unit detecting adsorption of the odor substance with respect to the substance absorption film, wherein the substance absorption film is a porous fine particle film that contains fine particles containing a compound having silicon and oxygen as a skeleton, and a surface modifier for modifying surfaces of the fine particles, and in at least a part of the plurality of sensor elements, compositions of the fine particles and/or the surface modifier are different from each other.

9 Claims, 13 Drawing Sheets

(52) U.S. Cl.
CPC ..... *G01N 33/0031* (2013.01); *G01N 33/0036* (2013.01); *G01N 2291/0215* (2013.01)

(56) References Cited

FOREIGN PATENT DOCUMENTS

| JP | 2010-60481 A | 3/2010 |
|----|--------------|--------|
| JP | 2011-102747 A | 5/2011 |
| JP | 2011-203008 A | 10/2011 |
| WO | WO2016/121155 A1 | 8/2016 |

OTHER PUBLICATIONS

International Search Report for PCT/JP2020/048945; mailed on Apr. 6, 2021.
Extended European Search Report for Application No. EP20904325.6, issued Nov. 17, 2023.
Office Action for Japanese Patent Application No. 2021-567710, issued Mar. 28, 2024.

\* cited by examiner

ODOR SENSOR, ODOR MEASUREMENT SYSTEM, AND METHOD FOR PRODUCING ODOR SENSOR

TECHNICAL FIELD

The present invention relates to an odor sensor for measuring an odor, an odor measurement system including the odor sensor, and a method for producing the odor sensor.

BACKGROUND ART

As an odor sensor, an odor sensor in which a polymer film is formed on the surface of a crystal oscillator is known (for example, Patent Document 1). In addition, it is known to change the type of skeleton polymer of the polymer film or the type of additive to be added to the skeleton polymer, in order to sense various odors.

CITATION LIST

Patent Document

Patent Document 1: JP-A-5-187986

SUMMARY OF THE INVENTION

Problem to be Solved by the Invention

In the odor sensor in which the polymer film is formed, the additive to be added to the skeleton polymer has been studied in order to sense more various odors. However, it may be difficult to add an additive that inhibits odor sensing performance of the skeleton polymer to the skeleton polymer.

The present invention has been made in consideration of the circumstances described above, and an exemplary object thereof is to provide an odor sensor capable of using an additive that was not capable of being adopted in an odor sensor including a polymer film, an odor measurement system using the odor sensor, and a method for producing the odor sensor.

Means for Solving the Problem

In order to attain the object described above, the present invention has the following configurations.

(1) An odor sensor including a plurality of sensor elements, the sensor element including: a substance absorption film adsorbing an odor substance; and a detection unit detecting adsorption of the odor substance with respect to the substance absorption film, in which the substance absorption film is a porous fine particle film that contains fine particles containing a compound having silicon and oxygen as a skeleton, and a surface modifier for modifying surfaces of the fine particles, and in at least a part of the plurality of sensor elements, compositions of the fine particles and/or the surface modifier are different from each other.

(2) An odor measurement system, including: the odor sensor according to any of the embodiments described herein, the odor sensor detecting an odor of an odor sample; and a data processing unit generating odor data in which each of electrical signals to be acquired from each of a plurality of sensor elements of the odor sensor and information of the odor sample are associated with each other.

(3) A method for producing an odor sensor including a plurality of sensor elements, the sensor element including: a substance absorption film adsorbing an odor substance; and a detection unit detecting adsorption of the odor substance with respect to the substance absorption film, the method including: a film disposing step of disposing a porous fine particle film that contains fine particles containing a compound having silicon and oxygen as a skeleton on detection surfaces of a plurality of detection units arranged adjacent to each other and covers the plurality of adjacent detection units; and a surface modifying step of applying a surface modifier for modifying surfaces of the fine particles onto a surface of the fine particle film, the surface modifiers with different compositions being applied for each predetermined region of the surface of the fine particle film.

Another object or other characteristics of the present invention will be apparent by the following preferred embodiments to be described with reference to the drawings.

Advantageous Effects of the Invention

According to the present invention, it is possible to provide an odor sensor capable of using an additive that was not capable of being adopted in an odor sensor including a polymer film, an odor measurement system using the odor sensor, and a method for producing the odor sensor.

DESCRIPTION OF THE EMBODIMENTS

Embodiment 1

Hereinafter, an odor sensor 10 according to Embodiment 1 will be described in order, with reference to the drawings.

In Embodiment 1, an "odor" can be acquired as olfactory information by a person or a living object including a person, and is a concept including the aggregation of a molecular simplex or a molecular group including different molecules, with each concentration.

In Embodiment 1, the aggregation of the molecular simplex or the molecular group including different molecules, with each concentration, which configures the odor described above, will be referred to as an "odor substance". Here, in a broad sense, the odor substance may broadly indicate a substance that can be adsorbed on a substance absorption film of an odor sensor described below. That is, a plurality of odor substances to be causation are usually included in the "odor", and there also can be a substance that is not recognized as the odor substance or an unknown odor substance, and thus, a substance that is not a causative substance of the odor can be generally included in the "odor".

<Odor Sensor 10>

Figure 1A:
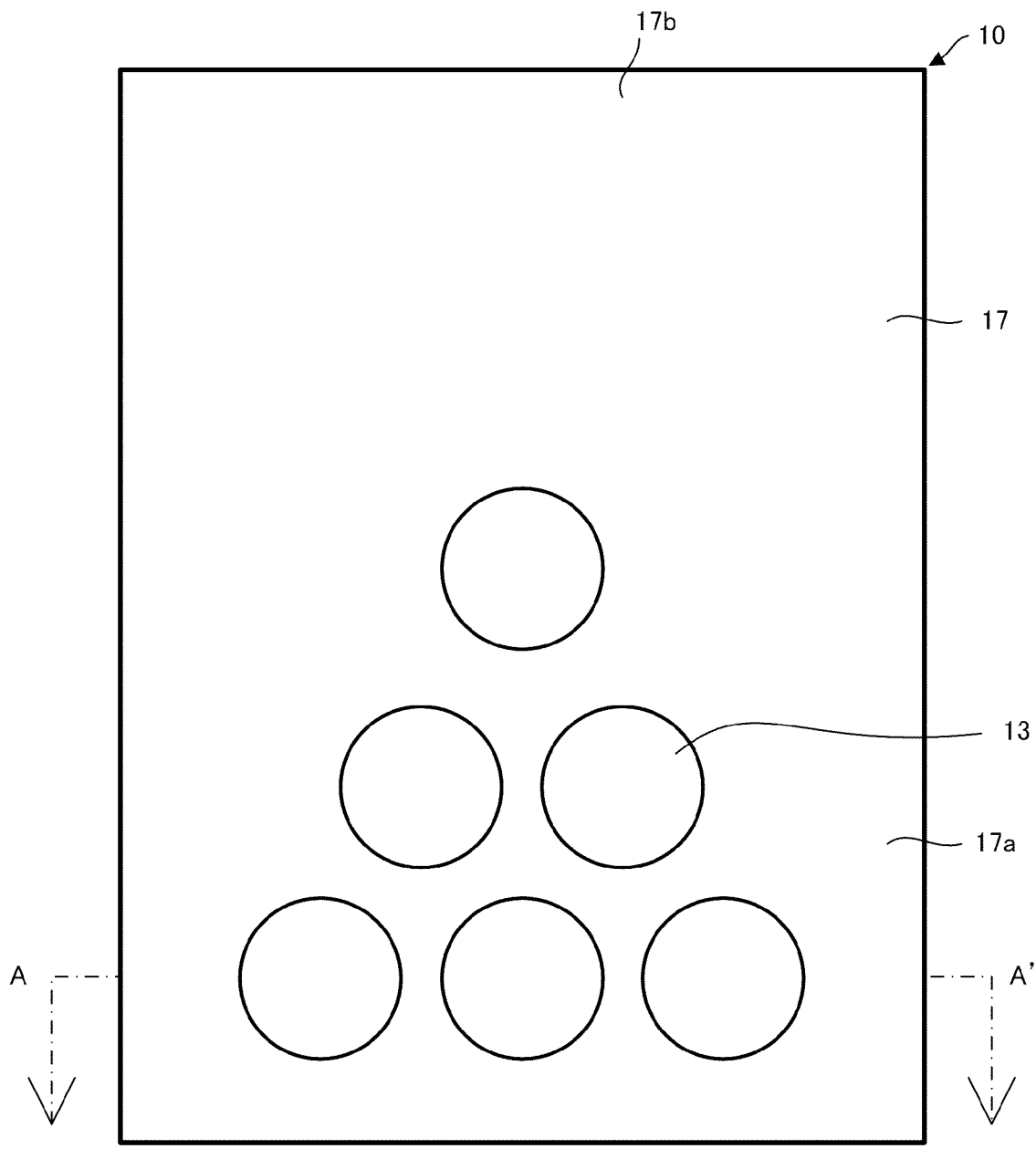
FIG. 1A is a plan schematic view of an odor sensor 10.
Figure 1B:
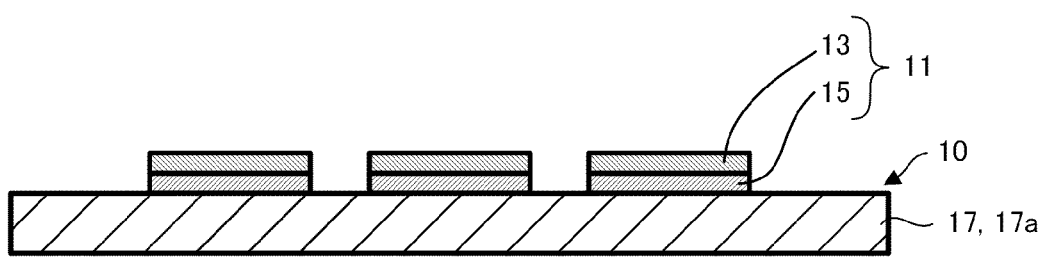
FIG. 1B is a sectional view of A-A' in FIG. 1A.

FIG. 1A is a plan schematic view of an odor sensor 10. FIG. 1B is a sectional view of A-A' in FIG. 1A. The odor sensor 10 is a sensor including a plurality of sensor elements 11 including a substance absorption film 13 adsorbing the odor substance, and a detector 15 as a detection unit detecting the adsorption of the odor substance with respect to the substance absorption film 13. The plurality of sensor elements 11 are disposed on a sensor substrate 17. Each of the sensor elements 11 is connected to an electronic circuit wired on the sensor substrate 17 (not illustrated in FIG. 1A and FIG. 1B).

As illustrated in FIG. 1A and FIG. 1B, the sensor element 11 includes the detector 15, and the substance absorption film 13 provided on the surface of the detector 15. It is preferable that the substance absorption film 13 covers the entire surface of the detector 15. That is, it is preferable that the size of the detector 15 is identical to a formation range of the substance absorption film 13 or less than the formation range of the substance absorption film 13. Note that, a plurality of detectors 15 may be provided in a formation range of one substance absorption film 13.

The plurality of sensor elements 11 are arranged on the sensor substrate 17, and as illustrated in FIG. 1A, six sensor elements 11 are may be aligned to draw an equilateral triangle. In this case, the substance absorption films 13 of the adjacent sensor elements 11 are not in contact with each other or insulated from each other. Note that, it is not necessary that the sensor elements 11 are aligned on the sensor substrate 17, and the sensor elements 11 may be randomly arranged, or may be aligned into an arbitrary shape.

It is preferable that in at least a part of the plurality of sensor elements 11 arranged on the sensor substrate 17, adsorption properties of each of the substance absorption films 13 with respect to the odor substance are different from each other. All of the plurality of sensor elements 11 may include the substance absorption films 13 having compositions different from each other, or there may not be the substance absorption films 13 having the same adsorption properties. The composition of the substance absorption film 13 can be changed in accordance with the composition of fine particles 21 described below, the composition of a surface modifier described below, the combination of the fine particles 21 and the surface modifier, and the like. That is, even the same odor substance (or an aggregate thereof) exhibits different adsorption properties with respect to the substance absorption films 13 having different adsorption properties. In FIG. 1A and FIG. 1B, for convenience sake, all of the substance absorption films 13 are similarly illustrated, but in practice, the adsorption properties thereof are different from each other. Note that, it is not necessary that the adsorption properties of all of the substance absorption films 13 of the respective sensor elements 11 are different from each other, and there may be the sensor elements 11 in which the substance absorption films 13 having the same adsorption properties are arranged.

<Substance Absorption Film 13>

Figure 2A:
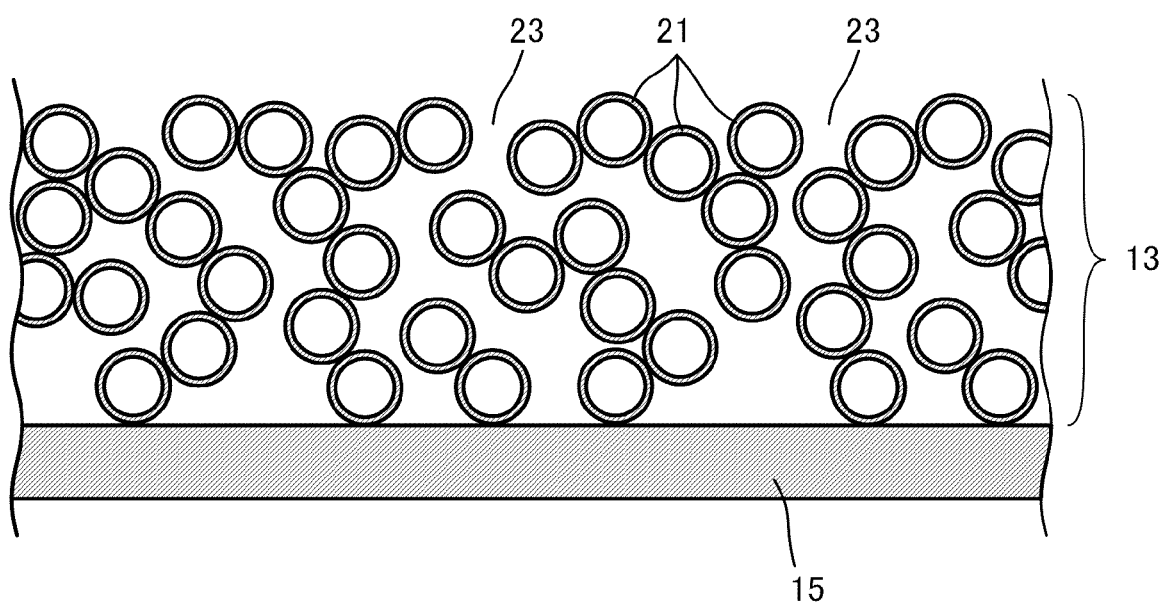
FIG. 2A is a sectional schematic view of a substance absorption film 13.

FIG. 2A is a sectional schematic view of the substance absorption film 13. The substance absorption film 13 is a fine particle film that contains fine particles 21 containing a compound having silicon and oxygen as a skeleton, and a surface modifier for modifying the surfaces of the fine particles 21. As illustrated in FIG. 2A, the substance absorption film 13 is a porous fine particle film in which a plurality of pores 23 are formed by a plurality of fine particles 21. The surfaces of the fine particles 21 are modified with the surface modifier. Note that, in FIG. 2A, a state in which the surfaces of the fine particles 21 are modified with the surface modifier is not illustrated. In Embodiment 1, the fine particles 21 are primary particles (particles that are not clumped).

The thickness of the substance absorption film 13 can be suitably selected in accordance with the properties of the odor substance to be an adsorption target. For example, the thickness of the substance absorption film 13 can be in a range of 10 nm to 10 m, and is preferably 50 nm to 800 nm. In a case where the thickness of the substance absorption film 13 is less than 10 nm, sufficient sensitivity may not be obtained. In addition, in a case where the thickness of the substance absorption film 13 is greater than 10 m, the weight of the substance absorption film 13 itself may be greater than an upper limit of a weight that can be detected by the detector 15.

<Fine Particles 21>

The fine particles 21 illustrated in FIG. 2A are hollow silica particles having voids inside. The fine particles 21 may be fine particles containing a compound having silicon and oxygen as a skeleton, and are not limited to the hollow silica particles. That is, the fine particles 21 are fine particles containing a compound mainly containing a silicon oxide, and are fine particles containing a compound having a skeleton having a Si—O—Si bond. Examples of the fine particles containing the compound having silicon and oxygen as a skeleton may include particles having a solid structure such as silica nanoparticles, silsesquioxane, siloxane, mesh-shaped silica, wire-shaped silica, or a wire-shaped or mesh-shaped nanosilica continuum, particles having a hollow structure such as hollow silica, mesoporous silica, nanoporous silica, or wire-shaped silica, particles having a microporous structure such as mesoporous silica, nanoporous silica, mesh-shaped silica, wire-shaped silica, or a wire-shaped or mesh-shaped nanosilica continuum, and the like. Note that, it is indicated that in the particles described above, the particles classified into a plurality of structures of the solid structure, the hollow structure, and the microporous structure are capable of having the structures, respectively. The shape of the fine particles 21 is not particularly limited, and may be a spherical shape, a rod shape, or an indefinite shape. The fine particles 21 may be crystalline fine particles, or may be amorphous fine particles.

Among various particles described above, the particles having the microporous structure and/or the hollow structure are preferable, and the particles having the microporous structure and the hollow structure are particularly preferable, as the fine particles 21. By using the fine particles 21 having the microporous structure and/or the hollow structure, the specific weight of the fine particles 21 decreases, and the weight of the substance absorption film 13 can be reduced. This is advantageous because detection sensitivity as the odor sensor 10 is improved in a case where the detector 15 detects a phenomenon associated with a weight change of the substance absorption film 13 due to the adsorption of the odor substance. For example, in a case where the detector 15 is a quartz crystal microbalance (QCM) sensor (hereinafter, also referred to as a "QCM sensor"), it is preferable that the weight of the substance absorption film 13 is 2% or less of the weight of a crystal oscillator of the QCM sensor.

Since the fine particles 21 have the microporous structure, a surface area increases, the surface that is modified with the surface modifier described below increases, and the effect of the surface modifier is easily obtained, which is advantageous. In addition, in a case where the fine particles 21 have the hollow structure, as described below, a substance for changing the properties of the fine particles 21, such as conductive fine particles, can be included, which is advantageous.

Figure 2B:
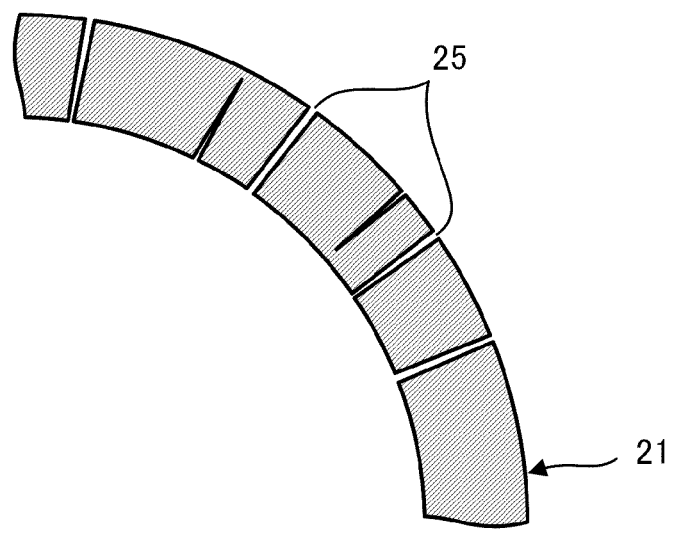
FIG. 2B is a sectional schematic view of fine particles 21.

FIG. 2B is a sectional schematic view of the fine particles 21. In Embodiment 1, micropores 25 indicate pores that are formed in the fine particles 21. The fine particles 21 in which the micropores 25 are formed may have a solid structure, or may have a hollow structure. On the other hand, the pores 23 indicate pores that are formed in the fine particle film (the substance absorption film 13) by the fine particles 21. In general, the pores indicate pores penetrating through a film or particles from one side to the other side, but in Embodiment 1, pores not penetrating through the film or the particles can also be included.

The size of the fine particles 21 is not particularly limited, and for example, the fine particles 21 having an average particle diameter of 2 nm to 1000 m can be used.

The fine particles 21 may contain conductive fine particles. The conductive fine particles may form the skeleton of the fine particles 21 together with silicon and oxygen, may be subsumed in the skeleton of the fine particles 21, or may be dispersed in the fine particles 21.

Figure 2C:
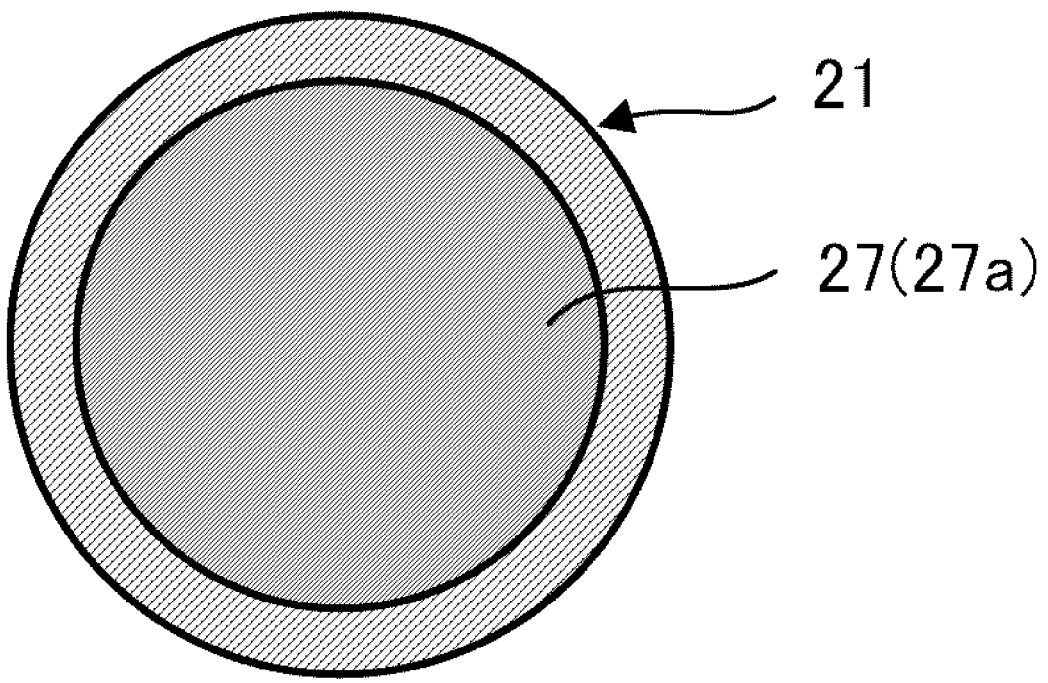
FIG. 2C is a sectional schematic view of the fine particles 21 to which conductive fine particles 27*a* are applied internally.
Figure 2D:
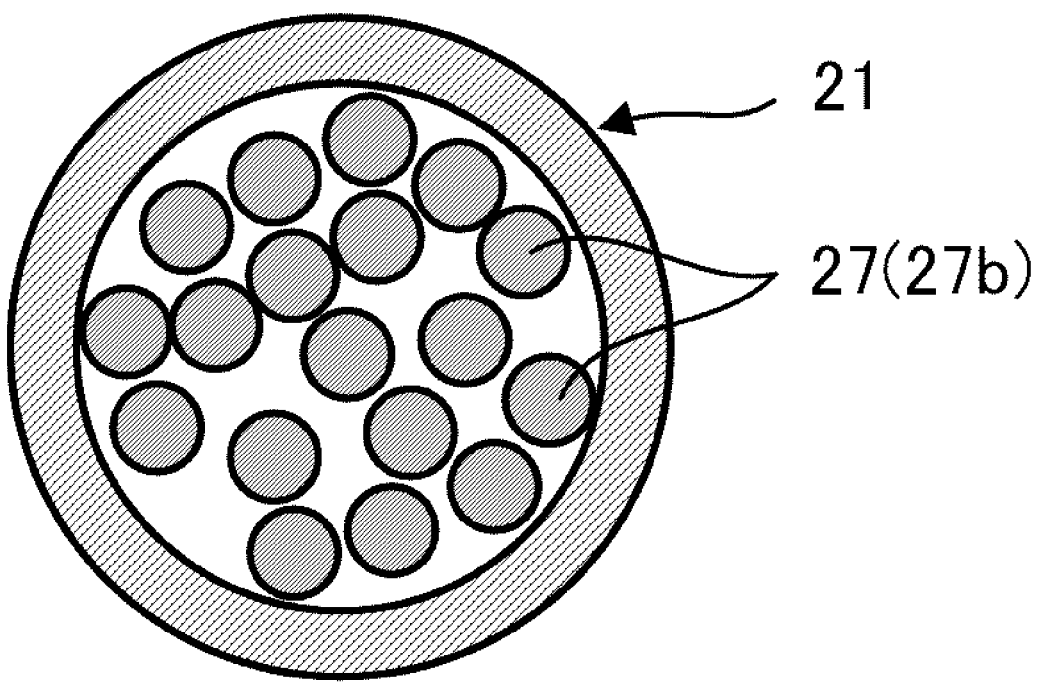
FIG. 2D is a sectional schematic view of the fine particles 21 to which conductive fine particles 27*b* are applied internally.

In a case where the fine particles 21 have the hollow structure, the conductive fine particles may be included in a hollow portion (a void portion). The conductive fine particles to be included in the hollow portion (the void portion) may be a single fine particle, or may be a plurality of fine particles. FIG. 2C is a sectional schematic view of the fine particles 21 to which conductive fine particles 27a are applied internally. FIG. 2D is a sectional schematic view of the fine particles 21 to which conductive fine particles 27b are applied internally.

The conductive fine particles are not particularly limited insofar as the conductive fine particles have conductivity, and examples thereof may include gold, silver, copper, aluminum, nickel, iron, platinum, palladium, tungsten, molybdenum, zinc, tin, carbon, conductive ceramic, and the like. The conductive fine particles to be contained or included in the fine particles 21 may be one type, may be two or more types, or may be an alloy of a plurality of metals of the metals described above.

In a case where the fine particles 21 are hollow particles in which the conductive fine particles are included, it is preferable that the substance absorption film 13 is combined with the detector 15 detecting a conductivity change described below. In a state where the hollow particles containing the conductive fine particles are in contact with each other, two conductive fine particles are capable of configuring a capacitor through the shell of the hollow particles. In a case where the odor substance is attached to the surfaces of the fine particles 21 that are modified with the surface modifier in such a state, a permittivity is changed, and the adsorption of the odor substance can be detected as the conductivity change.

<Surface Modifier>

The surface modifier is an additive that is added to the fine particles 21 in order to modify the surfaces of the fine particles 21. By changing the amount (the concentration), the type, or the like of the surface modifier to be added, the adsorption properties of the substance absorption film 13 with respect to the odor substance can be changed. The surface modifier is not particularly limited insofar as the surface modifier is capable of modifying surface physical properties of the fine particles 21 containing the compound having silicon and oxygen as a skeleton. The surface modifier may modify the surface physical properties of the fine particles 21 by reacting with the surfaces of the fine particles 21 and forming a chemical bond, or may modify the surface physical properties of the fine particles 21 by being physically attached to the surfaces of the fine particles 21. Examples of the surface modifier may include an inorganic acid such as a phosphoric acid and a boric acid, an organic acid such as formic acid, an acetic acid, a propionic acid, an octanoic acid, a palmitic acid, an oxalic acid, a succinic acid, a maleic acid, a fumaric acid, a p-toluene sulfonic acid, a 10-camphorsulfonic acid, a bis-2-ethyl hexyl sulfosuccinic acid, a methyl phosphonic acid, a chloromethyl phosphonic acid, a phenyl phosphonic acid, a methyl phosphine acid, and a di-2-ethyl hexyl phosphoric acid, an inorganic salt such as a dietary salt, an organic salt such as sodium lauryl sulfate and sodium laurate, an ionic liquid such as 1-ethyl-3-methyl imidazolium trifluoromethane sulfonate, a silane coupling agent such as dichlorodimethyl silane, trimethyl chlorosilane, methyl triethoxy silane, ethyl triethoxy silane, vinyl triethoxy silane, 3-aminopropyl triethoxy silane, butyl dimethyl chlorosilane, phenyl trimethoxy silane, nonafluorohexyl trimethoxy silane, octadecyl trimethyl chlorosilane, and heptadecafluorodecyl trimethoxy silane, an silanization agent such as 1,1,1,3,3,3-hexamethyl disilazane, tetramethyl silane, trimethyl (tridecafluorohexyl) silane, trimethyl silyl methoxy acetate, 2-(trimethyl silyl) pyridine, trimethyl (pentafluorophenyl) silane, 1,1,3,3-tetramethyl disilazane, 1-(dimethyl ethyl silyl) imidazole, and triisocyanate (methyl) silane, and the like. Such compounds may be used alone, or two or more types thereof may be used in combination.

In a case where the odor sensor 10 includes a detection sensor detecting the weight change as the detector 15, the surface modifier may be a compound reacting with a conductive polymer to decrease the conductivity of the conductive polymer. The conductive polymer may be used as a substance absorption film of an odor sensor of the related art, and an additive may be added in order to change physical properties thereof. In the odor sensor 10 including the detection sensor detecting the weight change as the detector 15, the fine particles 21 containing the compound having silicon and oxygen as a skeleton are used as a base material of the substance absorption film 13, and thus, even an additive that is considered difficult to adopt in the odor sensor of the related art, that is, the compound reacting with the conductive polymer to decrease the conductivity of the conductive polymer can be adopted without any particular difficulty. Examples of the compound reacting with the conductive polymer to decrease the conductivity of the conductive polymer may include an organic acid having a carboxyl group such as a formic acid, a propionic acid, a palmitic acid, an oxalic acid, a succinic acid, a maleic acid, and a fumaric acid, an organic acid having a sulfo group such as a p-toluene sulfonic acid, a 10-camphorsulfonic acid, and a bis-2-ethyl hexyl sulfosuccinic acid, an organic acid having a phosphoric acid group such as a methyl phosphonic acid, a chloromethyl phosphonic acid, a phenyl phosphonic acid, a methyl phosphine acid, and a di-2-ethyl hexyl phosphoric acid, and the like. In addition, examples of the compound reacting with the conductive polymer to decrease the conductivity of the conductive polymer may include organic acid derivatives and the like that generate the organic acids described above by hydrolysis or the like. Such organic acids may be used alone as the surface modifier, or two or more types thereof may be used in combination. In addition, the organic acid may have a plurality of functional groups described above, respectively. In a case where the organic acids have the plurality of functional groups described above, respectively, the type of functional group may be one type, or may be a combination of two or more types. In a case where the odor sensor 10 includes a detection sensor detecting a change in electrical properties as the detector 15, a conductor containing a carbon-based material, a nanometal material, or the like as a main component can be used as the surface modifier. In a case where the odor sensor 10 includes the detection sensor detecting the change in the electrical properties as the detector 15, it is possible to use the same surface modifier as that in a case of including the detection sensor detecting the weight change as the detector 15 by devising a detection method.

<Method for Preparing Substance Absorption Film 13>

Next, a method for preparing the substance absorption film 13 containing the fine particles 21 and the surface modifier will be described. The preparation of the substance absorption film 13 includes a film disposing step and a surface modifying step.

In the film disposing step, first, the porous fine particle film that contains the fine particles containing the compound having silicon and oxygen as a skeleton and covers the detector 15 is disposed on a detection surface of the detector 15. Specifically, a fine particle dispersion in which the fine particles 21 are dispersed in a solvent is applied. The solvent in which the fine particles 21 are dispersed is not particularly limited insofar as the fine particles 21 containing the compound having silicon and oxygen as a skeleton can be dispersed, and for example, water, ethanol, N-methyl pyrrolidone (NMP), and the like can be used. The thickness of the fine particle dispersion to be applied onto the surface of the detector 15 can be adjusted such that the thickness after drying is a predetermined thickness.

Next, the applied fine particle dispersion is dried. A drying condition is not particularly limited insofar as the solvent used for applying the fine particle dispersion is appropriately vaporized, and a structure of the fine particles 21 to be the base material of the substance absorption film 13 can be formed. As the drying condition, for example, heating can be performed at 100 C for 1.5 hours under an ordinary pressure.

Next, in the surface modifying step, the surface modifier for modifying the surfaces of the fine particles 21 is applied onto the surface of the fine particle film disposed in the film disposing step. Specifically, the surface modifier is applied to the structure of the fine particles 21 (the base material of the substance absorption film 13) that is obtained by drying. The amount of surface modifier to be applied is not particularly limited insofar as the surface modifier can be appropriately dispersed and applied to a desired range. For example, the surface modifier is diluted with a suitable solvent, and the diluted solvent is sprayed by using an ink jet apparatus or the like, and thus, the surface modifier can be applied to a desired range of the structure of the fine particles 21. The solvent for diluting the surface modifier is not particularly limited, and for example, water, ethanol, and the like can be used. The surface modifier may be applied to the entire structure of the fine particles 21, and can also be applied only to a desired part. In such a case, a different type of surface modifier can be applied to a part of the remaining portion or the entire remaining portion of the structure of the fine particles 21. In addition, the same surface modifier can be applied to a part of the remaining portion or the entire remaining portion of the structure of the fine particles 21 by changing a dilute concentration. In order to apply the surface modifier by changing the dilute concentration, for example, a movement rate of a nozzle of the ink jet apparatus, a spray amount, the number of times for spraying, and the like can be adjusted.

Next, the structure of the fine particles 21 to which the surface modifier is applied is dried. A drying condition is not particularly limited insofar as the solvent used for diluting the surface modifier is appropriately vaporized, and the surfaces of the fine particles 21 are appropriately modified with the surface modifier. As the drying condition, for example, heating can be performed at 100 C for 1 hour under an ordinary pressure.

The amount of surface modifier to be applied (added) to the fine particles 21 is not particularly limited insofar as the surfaces of the fine particles 21 can be modified.

<Detector 15 (Detection Unit)>

The detector 15 has a function as a detection unit or a signal conversion unit (a transducer) that detects a phenomenon associated with a change in physical, chemical, and electrical properties of the substance absorption film 13 due to the odor substance adsorbed on the surface of the substance absorption film 13, and outputs measurement data, for example, as an electrical signal. That is, the detector 15 is a detection sensor detecting an adsorption state of the odor substance with respect to the surface of the substance absorption film 13. Examples of the signal that is output by the detector 15 as the measurement data include an electrical signal, light, and the like, and information such as a change in electrical resistance and a change in an oscillation frequency is output with such a signal.

The detector 15 is not particularly limited insofar as the phenomenon associated with the change in the physical, chemical, electrical properties, and the like of the substance absorption film 13 can be detected, and various detection sensors can be suitably used. Examples of the change in the physical, chemical, and electrical properties to be detected by the detector 15 may include the weight change of the substance absorption film 13 and the change in the electrical properties such as the conductivity due to the odor substance adsorbed on the surface of the substance absorption film 13.

Specifically, examples of the detector 15 may include a detection sensor detecting a weight change, such as a quartz crystal microbalance (QCM) sensor, a microelectromechanical system (MEMS) sensor, a cantilever type sensor, and a surface acoustic wave (SAW) sensor, a detection sensor detecting a change in electrical properties, such as a field-effect transistor (FET) sensor, a charge-coupled device sensor, a MOS field-effect transistor sensor, a metal-oxide-semiconductor sensor, a complementary metal oxide semiconductor (CMOS) sensor, an organic conductive polymer sensor, and an electrochemical sensor, and the like. Among them, the quartz crystal microbalance (QCM) sensor and the like are preferable as the detection sensor detecting the weight change, and the complementary metal oxide semiconductor (CMOS) sensor and the like are preferable as the detection sensor detecting the change in the electrical properties. Hereinafter, a case of using the quartz crystal microbalance (QCM) sensor (hereinafter, also referred to as a "QCM sensor") as the detector 15 will be described.

<Quartz Crystal Microbalance (QCM) Sensor>

In a case of using the QCM sensor as the detector 15, an electrode can be provided on both surfaces of a crystal oscillator as an exciting electrode. In order to detect a high Q value, a separate electrode may be provided on one surface. In addition, the exciting electrode may be provided on the crystal oscillator on the sensor substrate 17 side across the sensor substrate 17. Note that, in FIG. 1B, the crystal oscillator is illustrated as the detector 15, and the exciting electrode is not illustrated.

The exciting electrode can be formed of an arbitrary conductive material. Specifically, examples of the material of the exciting electrode may include an inorganic material such as gold, silver, platinum, chromium, titanium, aluminum, nickel, a nickel-based alloy, silicon, carbon, and a carbon nanotube, and an organic material such as a conductive polymer such as polypyrrole and polyaniline.

The shape of the detector 15 can be a flat shape as illustrated in FIG. 1A and FIG. 1B. The shape of a flat surface of the flat shape can be a circular shape as illustrated in FIG. 1A, and may be various shapes such as a quadrangular shape or a square shape, and an elliptical shape. In addition, the shape of the detector 15 is not limited to the flat shape, and the thickness thereof may be changed, or a concave portion or a convex portion may be formed.

In a case where an oscillator such as a crystal oscillator sensor is used in the detector 15, a resonance frequency of each of the oscillators in the plurality of sensor elements 11 is changed, and thus, the influence (the crosstalk) of other oscillators coexisting on the same sensor substrate 17 can be reduced. The resonance frequency can be arbitrarily designed such that each of the oscillators on the same sensor substrate 17 exhibits different sensitivities with respect to a certain oscillation frequency. The resonance frequency, for example, can be changed by adjusting the thickness of the oscillator or the substance absorption film 13.

<Sensor Substrate 17>

The sensor substrate 17 is a substrate on which the detector 15 and the substance absorption film 13 on the surface of the detector 15 can be disposed. A silicon substrate, substrate containing quartz crystals, a printed-wiring substrate, a ceramic substrate, a resin substrate, and the like can be used. In addition, the substrate is a multi-layer wiring substrate such as an interposer substrate, and wiring for allowing each of the plurality of detectors 15 to function, such as the exciting electrode for oscillating the crystal oscillator and an electrode for mounting wiring and energizing, is disposed in an arbitrary position.

As illustrated in FIG. 1A, the region of the sensor substrate 17 is divided into a sensor portion 17a in which the plurality of sensor elements 11 are disposed, and a retaining portion 17b in which the sensor element and the like are not disposed on the surface. Since the sensor element and the like are not disposed on the surface of the retaining portion 17b, a person is capable of retaining the retaining portion 17b with fingers, tweezers, or the like. Accordingly, the odor sensor 10 can be a chip that is detachable with respect to an odor measurement device as an odor measurement system 1 described below.

According to the configuration as described above, it is possible to obtain the odor sensor 10 including the plurality of sensor elements 11 including the substance absorption films 13 having different adsorption properties of the odor substance. Accordingly, in a case of measuring the odor of the air containing a certain odor substance or the composition thereof with the odor sensor 10, the odor substance or the composition thereof is similarly in contact with the substance absorption films 13 of each of the sensor elements 11, but the odor substance is adsorbed in each of the substance absorption films 13 in manners different from each other. That is, in each of the substance absorption films 13, an adsorption amount of the odor substance is different. Accordingly, in each of the sensor elements 11, a detection result of the detector 15 is different. Therefore, the measurement data of the detector 15 with respect to the certain odor substance or the composition thereof is generated for the number of sensor elements 11 (substance absorption films 13) of the odor sensor 10.

A set of the measurement data to be generated by the odor sensor 10 by measuring the certain odor substance or the composition thereof is generally unique to a specific odor substance or the composition of the odor substance. Accordingly, the odor can be identified as a single odor substance or the composition (a mixture) of the odor substance by measuring the data with the odor sensor 10.

<Odor Measurement System 1>

Figure 3:
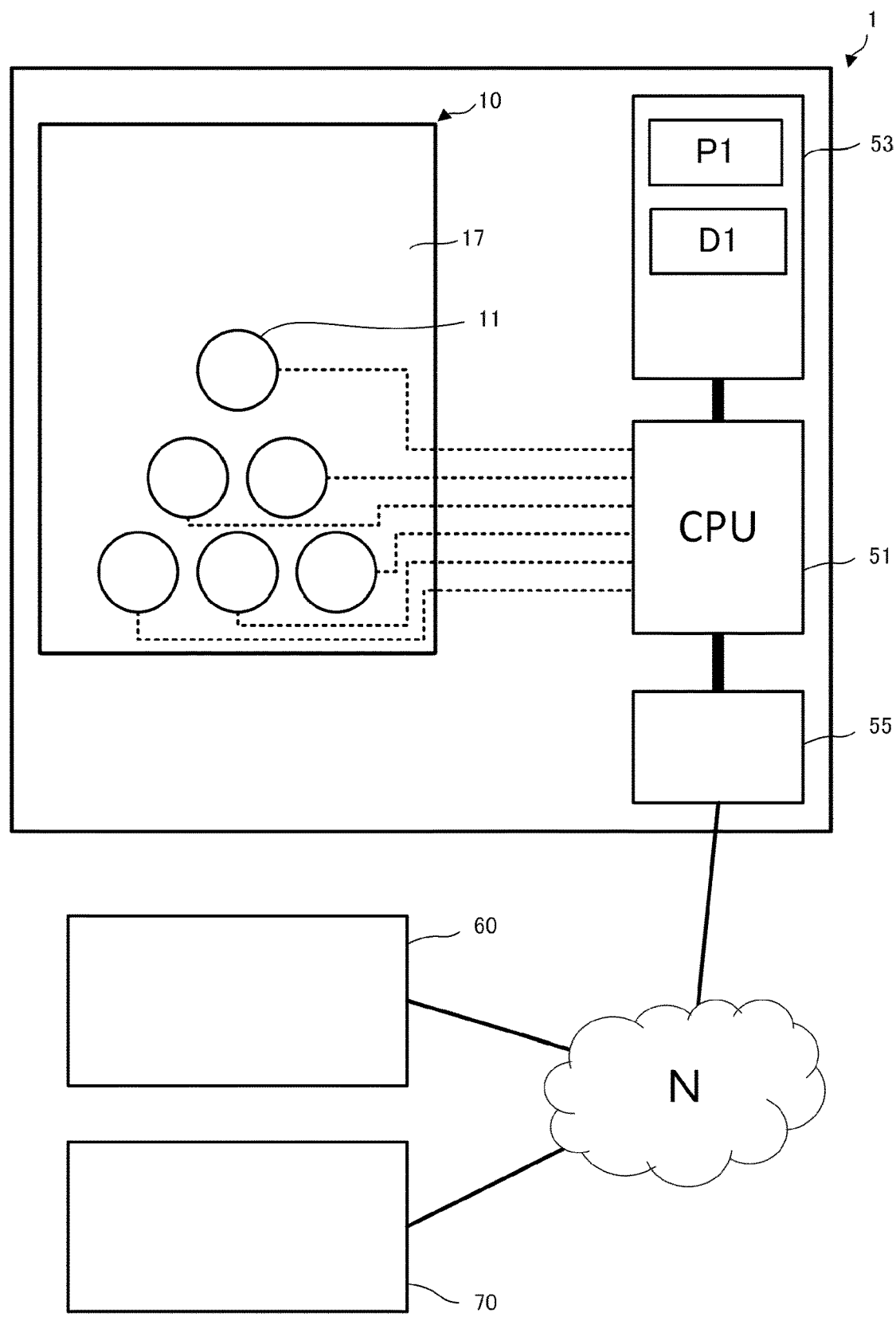
FIG. 3 is a schematic view of an odor measurement system 1.

The odor measurement system 1 includes the odor sensor 10 described above, and a data processing unit, and generates odor data on the basis of the odor of an odor sample that is detected by the odor sensor 10. The data processing unit generates the odor data in which each of the electrical signals to be acquired from each of the plurality of sensor elements 11 of the odor sensor 10 and the information of the odor sample are associated with each other. The data processing unit includes at least a central processing unit (CPU) 51 and a storage unit 53. FIG. 3 is a schematic view of the odor measurement system 1.

Specifically, the odor measurement system 1 can be an information processing terminal including the odor sensor 10. Examples of the information processing terminal may include a computer, a tablet type terminal, a smart phone, a mobile phone, and the like. In addition, the odor measurement system 1 can be attained by combining an information processing terminal including a reading unit that is capable of reading a detection signal of the chip type odor sensor 10, the central processing unit (CPU) 51, and the storage unit 53 with the chip type odor sensor 10.

As illustrated in FIG. 3, the detector 15 of each of the sensor elements 11 of the odor sensor 10 is connected to the central processing unit (CPU) 51 of the data processing unit by internal wiring of the sensor substrate 17 such that communication can be performed to each other. Accordingly, the signal detected by the detector 15 is transmitted to the central processing unit 51.

The central processing unit (CPU) 51 has a function of generating the odor data on the basis of the acquired signal. Such a function is attained by the central processing unit (CPU) 51 executing an odor data generating program P1 stored in the storage unit 53 that is connected to the central processing unit (CPU) 51 such that communication can be performed to each other. In the odor data, for example, an ID or a name as the information of the odor sample, and the data detected in each of the sensor elements 11 are associated with each other. The data detected in each of the sensor elements 11 can be digitized by the odor data generating program P1, in accordance with predetermined processing. The generated odor data, for example, can be stored in the storage unit 53, as an odor database Dl.

<Odor Identification System>

The odor measurement system 1 may configure a part of an odor identification system that outputs whether or not the odor measured by the odor measurement system 1 is coincident with known odor data or a similarity to the known odor data. As illustrated in FIG. 3, the odor identification system, for example, can be configured by an odor data server 60 that is connected to the odor measurement system through the internet N such that communication can be performed to each other. The odor measurement system 1 may include a communication unit 55 to be connected to the other information processing terminal such that communication can be performed to each other, or may be connected to the odor data server 60 by using the communication unit 55. As illustrated in FIG. 3, the odor identification system may include a sensor arrangement information server 70 that is connected through the internet N such that communication can be performed to each other. Note that, the odor data server 60 and the sensor arrangement information server 70 may not be connected through the internet N, or may be connected such that communication can be performed to each other in an intranet or in the odor measurement system 1.

In the odor data server 60, the known odor data can be accumulated and stored. For example, the odor data measured by using the odor measurement system 1 can be transmitted to the odor data server 60 and stored.

By comparing the odor data obtained by the measurement of the odor measurement system 1 with the known odor data stored in the odor data server 60, whether or not the odor data obtained by the measurement is coincident with the known odor data, the similarity to the known odor data, or the like can be output.

In the sensor arrangement information server 70, arrangement information of the plurality of sensor elements 11 in the odor sensor 10 can be stored. The arrangement information may include at least position information of each of the sensor elements 11 in the odor sensor 10 and composition information of the substance absorption film 13 formed in the sensor element 11. The composition information of the substance absorption film 13 can be composition information of the base material (the fine particles 21) of the substance absorption film 13 and composition information of the additive (the surface modifier).

By using the sensor arrangement information server 70, the substance absorption film 13 formed in each of the sensor elements 11 of the odor sensor 10 can be changed for each odor sensor 10, and thus, the type of substance absorption film 13 (the type of composition) can be increased. That is, the odor data measured by the specific odor sensor 10 can be uniquely specified by combining the odor data obtained by the measurement of the odor measurement system 1 including the specific odor sensor 10 with the arrangement information of the specific odor sensor 10 that is stored in the sensor arrangement information server 70. By comparing the odor data specified as described above with the known odor data stored in the odor data server 60, whether or not the odor data obtained by the measurement is coincident with the known odor data, the similarity to the known odor data, or the like can be output.

Embodiment 2

As Embodiment 2, an odor sensor 100 in which a plurality of sensor elements 111 are arranged such that detectors 115 as the detection unit are adjacent to each other will be described. Note that, configurations not mentioned in the following description of Embodiment 2 are identical to the configurations of the odor sensor 10 according to Embodiment 1, and the same reference numerals are used.

Figure 4A:
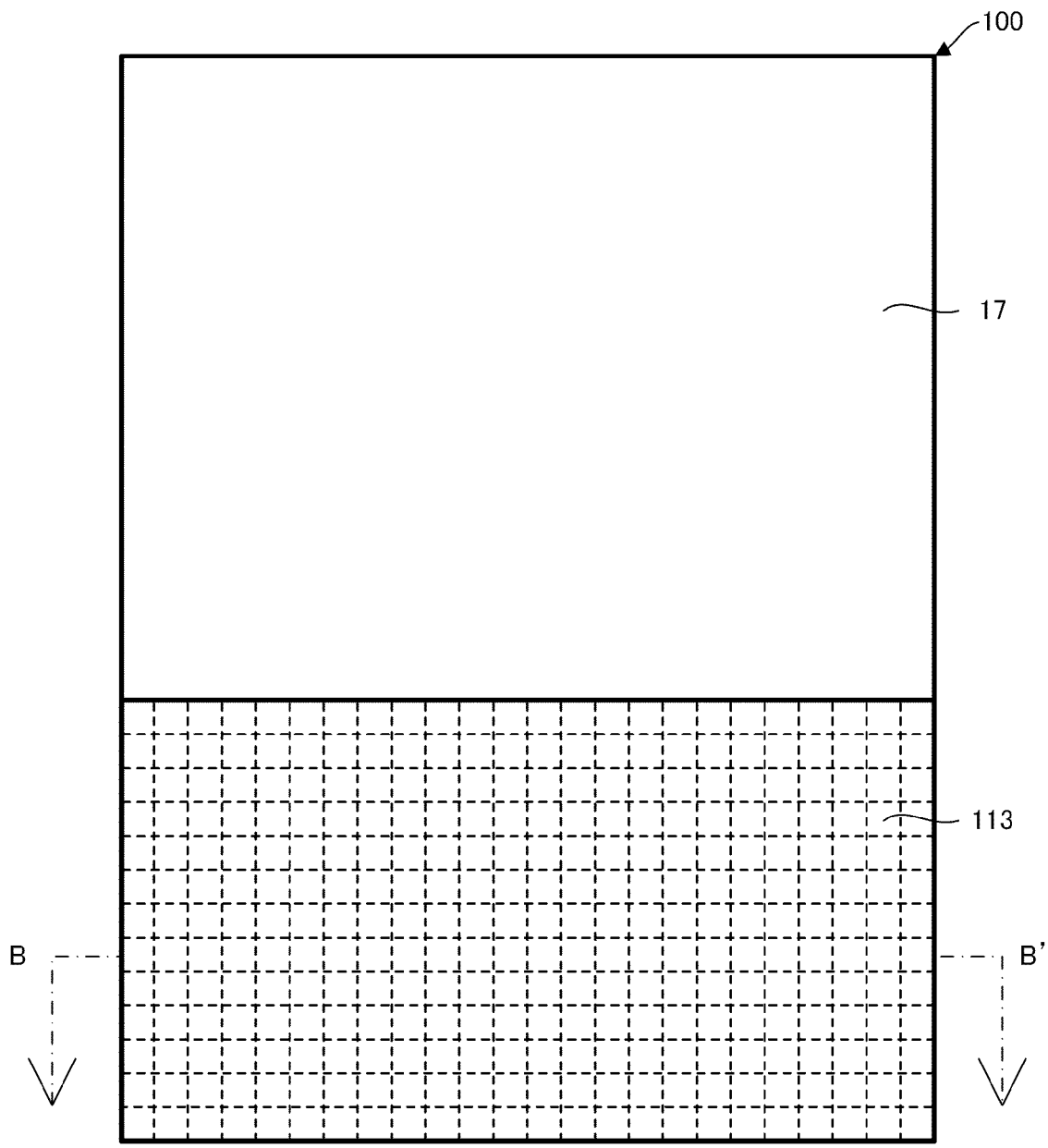
FIG. 4A is a plan schematic view of an odor sensor 100.
Figure 4B:
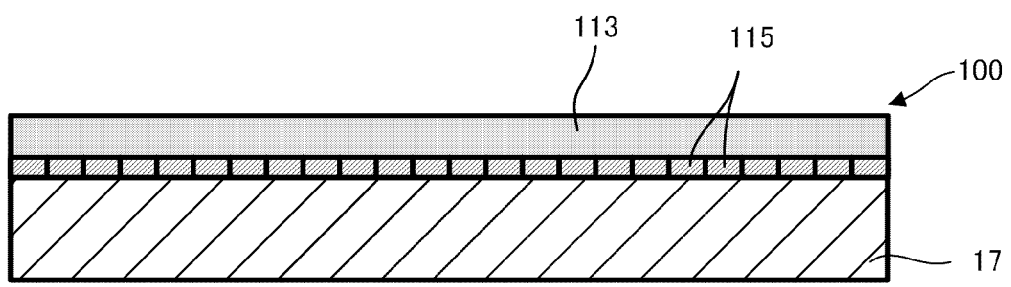
FIG. 4B is a sectional view of B-B' in FIG. 4A.

FIG. 4A is a plan schematic view of the odor sensor 100. FIG. 4B is a sectional view of B-B' in FIG. 4A. In the odor sensor 100, each of the detectors 115 are arranged adjacent to each other on the sensor substrate 17. A substance absorption film 113 is formed on the surfaces of the detectors 115 that are arranged adjacent to each other, and the detectors 115 that are arranged adjacent to each other are covered with the substance absorption film 113. The substance absorption film 113 is shared in a plurality of adjacent detectors 115 of the plurality of sensor elements 111 that are adjacent to each other. That is, in FIG. 4A and FIG. 4B, the single substance absorption film 113 is formed on the surfaces of all of the detectors 115 that are arranged adjacent to each other. In this case, the surface modifier to be added (applied) to the fine particles 21 that are the base material is not changed for each single detector 115, and the surfaces of the fine particles 21 are modified with one type of surface modifier in a range for covering the plurality of detectors 115.

It is preferable that the detector 115 is a detector detecting a conductivity change of the substance absorption film 113 due to the adsorption of the odor substance. Note that, in a case of a detector detecting a weight change of the substance absorption film 113, the substance absorption film 113 is shared with other detectors 115, and thus, there may be a case where the weight change is not capable of being accurately detected.

Specifically, as the detector 115, a field-effect transistor (FET) sensor, a charge-coupled device sensor, a MOS field-effect transistor sensor, a metal-oxide-semiconductor sensor, a complementary metal oxide semiconductor (CMOS) sensor, an organic conductive polymer sensor, an electrochemical sensor, and the like are preferable, and among them, the complementary metal oxide semiconductor (CMOS) sensor is particularly preferable.

<Method for Producing Odor Sensor 100>

The substance absorption film 113 of the odor sensor 100 can be prepared by a film disposing step of the detector 115 with respect to a detection surface and a surface modifying step. A method for preparing a configuration other than the substance absorption film 113 of the odor sensor 100 is not particularly limited, and the configuration can be prepared on the basis of known methods of the related art or the method for preparing the odor sensor 10.

In the film disposing step of the substance absorption film 113, a porous fine particle film that contains the fine particles 21 and covers the plurality of adjacent detectors 115 is disposed on the detection surfaces of the plurality of detectors 115 arranged adjacent to each other. Note that, such a film disposing step is identical to the film disposing step in the method for preparing the substance absorption film 13 except that the detectors 115 are arranged adjacent to each other.

In the surface modifying step of the substance absorption film 113, the surface modifier is applied onto the surface of the fine particle film disposed in the film disposing step. In this case, the surface modifying step of the substance absorption film 113 is different from the surface modifying step in the method for preparing the substance absorption film 13 in that the surface modifiers having different compositions are applied for each predetermined region of the surface of the fine particle film. Here, the plurality of detectors 115 are disposed on a lower layer of the fine particle film in a predetermined region, and such detectors 115 share the substance absorption film 113 in at least the predetermined region.

Figure 5:
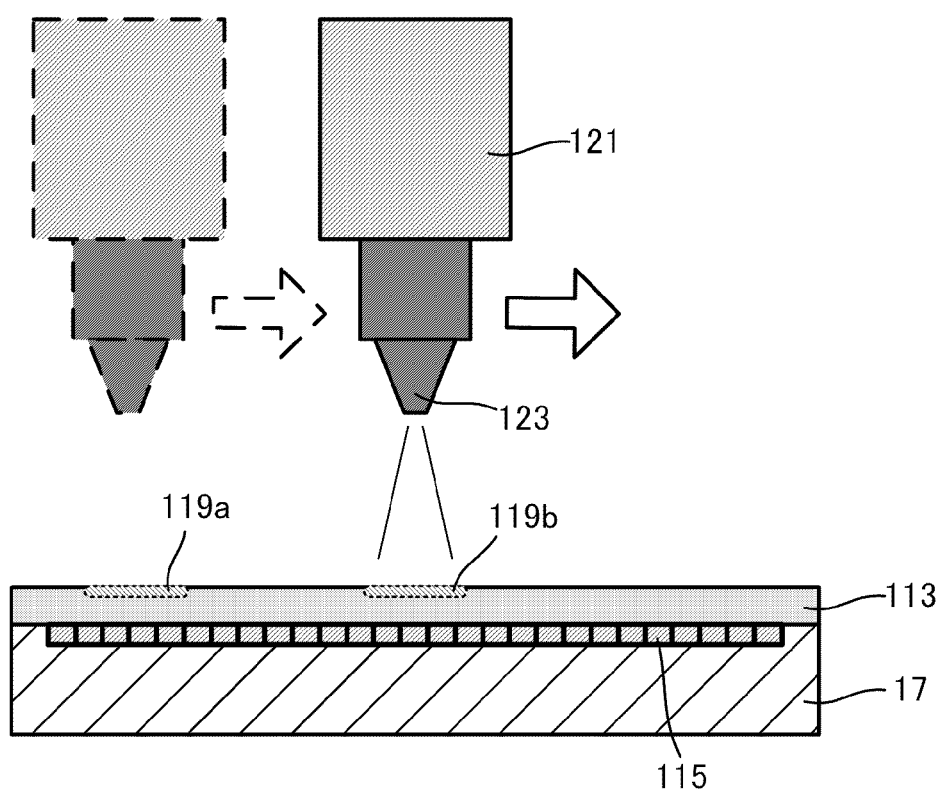
FIG. 5 is an explanatory diagram illustrating outline of a method for producing the odor sensor 10.

FIG. 5 is an explanatory diagram illustrating the outline of a method for producing the odor sensor 10. In the surface modifying step of a method for producing the odor sensor 100, an ink jet spray apparatus can be used as illustrated in FIG. 5. That is, the surface modifier to be applied to the fine particle film is sprayed from an ink jet nozzle 123, and thus, the surface modifier can be applied to a predetermined region 119a of the surface of the fine particle film. Then, in order to spray the surface modifier to a next predetermined region 119b, the surface modifier can be sprayed by moving an ink jet head 121 to the next predetermined region 119b along the substance absorption film 113. In this case, it is preferable that the surface modifier to be sprayed to the next predetermined region 119b has a composition different from that of the surface modifier sprayed to the first predetermined region 119a.

The predetermined regions 119a and 119b may be consecutive. That is, the spray is started from the predetermined region 119a, and the ink jet head 121 is moved along the substance absorption film 113 while spraying the surface modifier, and thus, the surface modifier can be applied to a wide range of the fine particle film. In addition, the surface modifier having a different composition is further applied to a region to which the surface modifier is already applied, and thus, it is possible to form a region to which two types of surface modifiers are applied. In addition, when moving the ink jet head 121 while spraying the surface modifier, a region in which the amount of surface modifier to be applied is continuously changed may be formed by adjusting a spray amount.

Embodiment 3

<Odor Sensor Arrangement>

Next, as Embodiment 3, an odor sensor arrangement 205 will be described. Note that, configurations not mentioned in the following Embodiment 3 are identical to the configurations of the odor sensor 10 according to Embodiment 1, and the same reference numerals are used.

Figure 6:
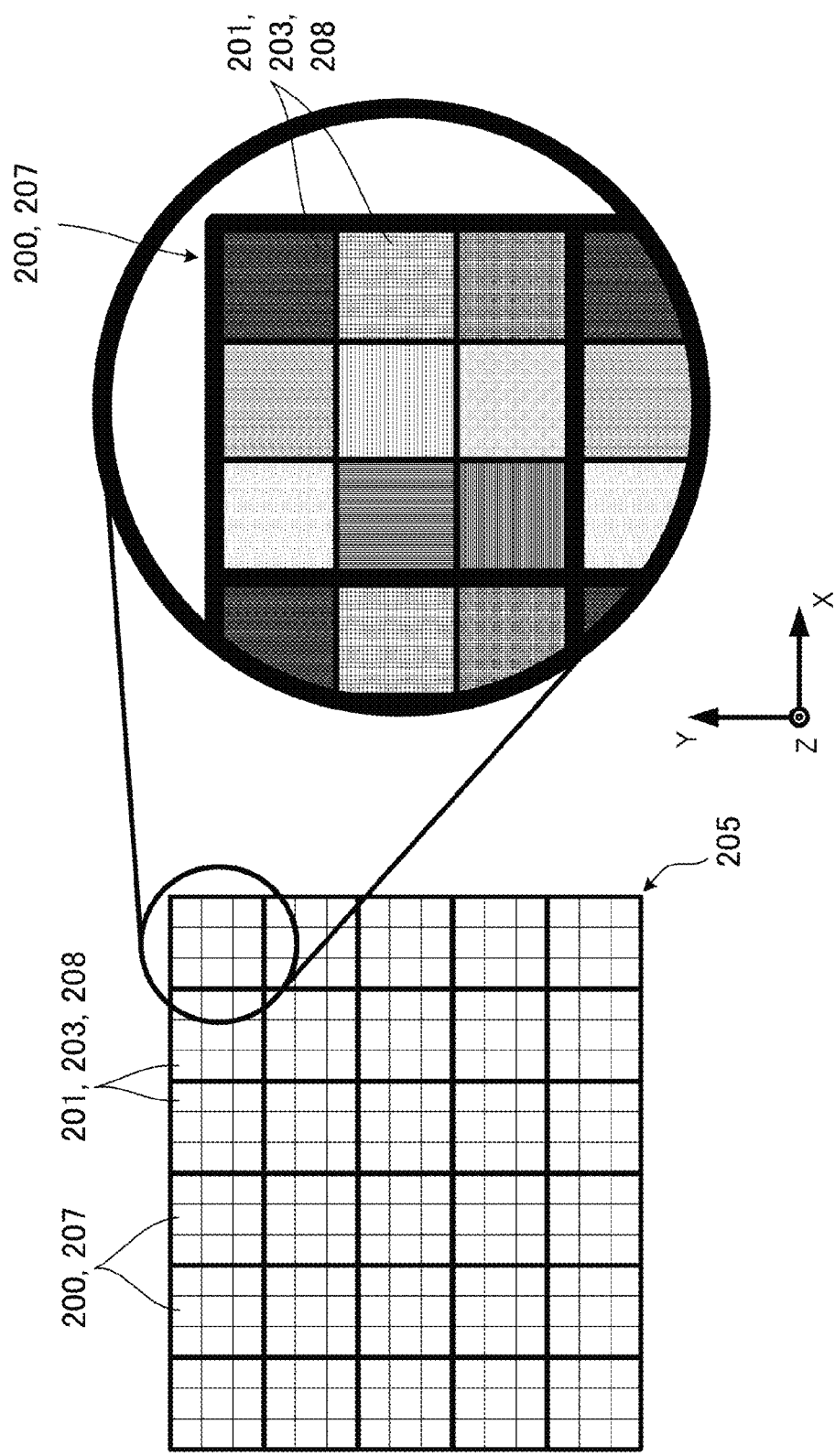
FIG. 6 is a schematic view of an odor sensor arrangement 205 and a partially enlarged view thereof.

FIG. 6 is a schematic view of the odor sensor arrangement 205 and a partially enlarged view thereof. In FIG. 6, a partially enlarged view including an odor sensor 200 disposed on the most upper right of the odor sensor arrangement 205 and the vicinity thereof is illustrated in a circle. In FIG. 6, a case is illustrated in which a total of 30 odor sensors 200 in which nine sensor elements are arranged into the shape of a plane including three sensor elements in a Y direction and three sensor elements in an X direction are arranged into the shape of a plane including five odor sensors in the Y direction and six odor sensors in the X direction. In each of the odor sensors 200, nine sensor elements 201 include substance absorption films 203 different from each other.

In the odor sensor arrangement 205, two or more odor sensors 200 including the sensor elements 201 are arranged. As the odor sensor 200, the same odor sensor as the odor sensor 10 described in Embodiment 1 can be used, and the odor sensor 200 includes two or more sensor elements 201 including the substance absorption film 203 adsorbing the odor substance and a detection unit determining an adsorption state of the odor substance with respect to the substance absorption film 203. Each of the substance absorption films 203 of two or more sensor elements has adsorption properties different from each other.

In the odor sensor arrangement 205, the two or more odor sensors described above are arranged, and thus, the adsorption state of the odor substance in two or more different positions can be sensed. Accordingly, it is possible to sense position information of the odor substance or a gas containing the odor substance.

In the two or more different positions, an adsorption amount of the odor substance with respect to the substance absorption film 203 can be measured, and thus, a movement direction of the odor substance or the gas containing the odor substance can be grasped on the basis of a difference in the adsorption amount of the odor substance in each of the odor sensors. That is, the movement direction of the odor substance can be sensed. For example, a so-called "burnt smell" or the like that occurs in a smoldering state before ignition is sensed in the odor sensor arrangement 205, and thus, it is possible to sense from which direction the burnt smell is moved, which may contribute to the specification of the fire origin.

In addition, a measured value of each of the odor sensors of the odor sensor arrangement 205 can be recorded in chronological order. Accordingly, it is possible to grasp a process in which the odor substance is moved over time. It is obvious that a concentration distribution of the odor substance in a position corresponding to each of the odor sensors of the odor sensor arrangement 205 and a transition process thereof can also be grasped.

The odor sensors 200 included in the odor sensor arrangement 205 may be identical to or different from each other, and in a case of grasping a movement direction of a specific odor substance, it is preferable that at least one type of substance absorption film 203 of each of the odor sensors 200 is commonly provided in each of the odor sensors 200. In addition, it is more preferable that a combination of the substance absorption films 203 of each of the odor sensors 200 is commonly provided in each of the odor sensors 200. Further, it is preferable that the odor sensors 200 are identical to each other.

The entire shape of the odor sensor arrangement 205 is not particularly limited, and for example, as illustrated in FIG. 6, the odor sensor arrangement 205 may be a flat odor sensor arrangement 205 in which the respective sensor elements 201 of the respective odor sensors are arranged into the shape of a plane, and the respective odor sensors 200 are arranged into the shape of a plane. In a case where the entire shape of the odor sensor arrangement 205 is a flat shape, it is easy to provide the odor sensor arrangement 205 in an arbitrary planar place such as a wall, a ceiling, and a floor.

The entire shape of the odor sensor arrangement 205 may be a cylindrical shape or a spherical shape in which the surface is covered with the odor sensor 200. As described above, by setting the entire shape to the cylindrical shape or the spherical shape, the movement direction of the odor substance can be three-dimensionally grasped.

A method for producing the odor sensor arrangement 205 is not particularly limited, and the detection surface of the detector 15 is divided into sections 207 in a range corresponding to the odor sensor, and small fractions 208 in a range corresponding to the sensor element 201 in the section 207, and then, different substance absorption films 203 can be formed in the small fractions 208, respectively.

Hereinafter, the odor sensor will be described in more detail by using Examples.

Example 1

In an odor sensor including the substance absorption film 13 containing nickel particles coated with silica as the fine particles 21 and an octanoic acid as the surface modifier (hereinafter, an "odor sensor A") as the odor sensor 10 according to Embodiment 1, reaction properties with respect to ammonia were checked. Here, the nickel particles coated with silica are fine particles in which nickel particles as the conductive fine particles 27a are covered with a silica film in the fine particles 21 as illustrated in FIG. 2C. The detector 15 of the odor sensor A was a QCM sensor.

Figure 7:
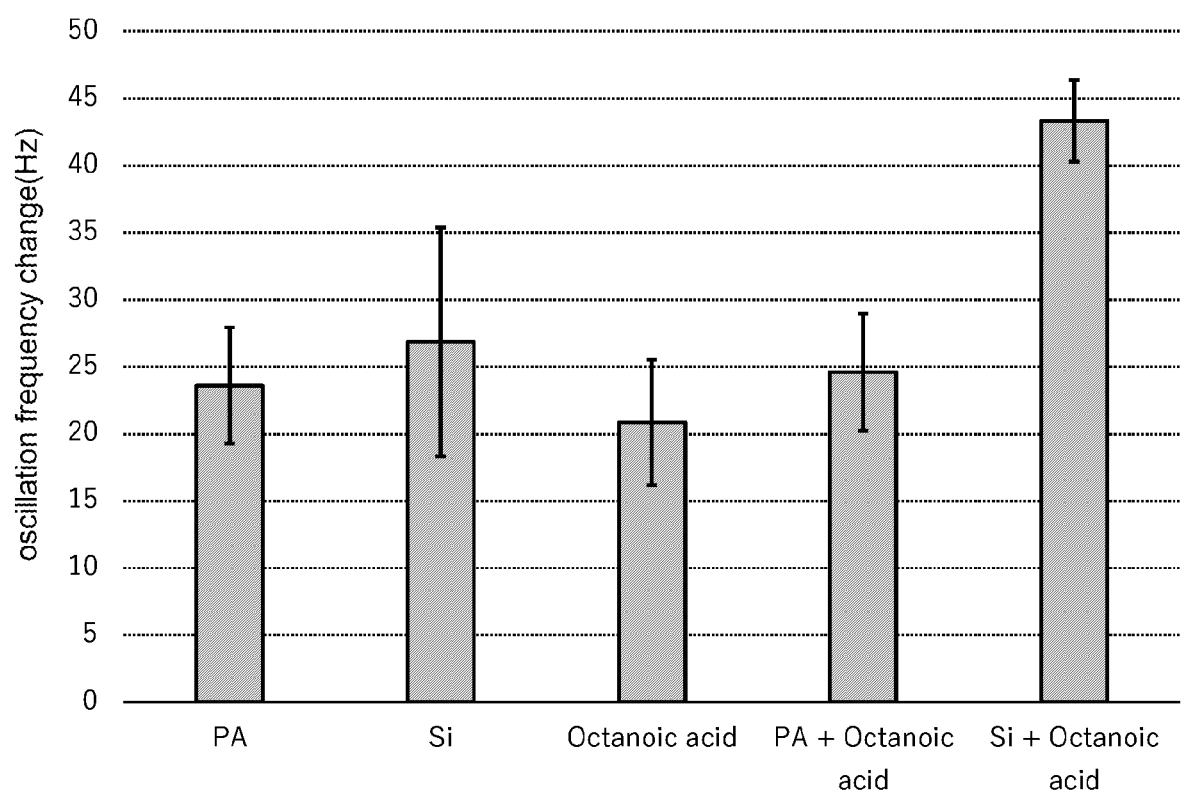
FIG. 7 is a graph illustrating reaction properties of an odor sensor A.

A graph illustrating the reaction properties of the odor sensor A with respect to ammonia is illustrated in FIG. 7. In FIG. 7, a vertical axis indicates an oscillation frequency change (Hz) to be detected by the QCM sensor as a reaction when the odor sensor measures ammonia. Each of bar graphs in FIG. 7 illustrates the oscillation frequency change of the odor sensor in a case where the substance absorption film is a polyaniline film ("PA" in FIG. 7), a film to which only the nickel particles coated with silica (not containing the surface modifier) are applied ("Si" in FIG. 7), a film to which only the octanoic acid that is the surface modifier is applied ("Octanoic acid" in FIG. 7), a film to which a mixture of polyaniline and the octanoic acid is applied ("PA+Octanoic acid" in FIG. 7), and a film to which a mixture of the nickel particles coated with silica and the octanoic acid is applied ("Si+Octanoic acid" in FIG. 7), in order from the left.

In FIG. 7, the result of "Si+Octanoic acid" is the result of the odor sensor A. In the odor sensor A including the substance absorption film 13 containing the nickel particles coated with silica of which the surfaces are modified with the octanoic acid, the amount of oscillation frequency change was significantly large, compared to "Si" of which the surface is not modified and "Octanoic acid" not containing the fine particles 21. In addition, in the odor sensor A, the amount of oscillation frequency change was also significantly large, compared to "PA" including a known polyaniline film of the related art and "PA+Octanoic acid" in which the octanoic acid is added to polyaniline.

Example 2

In an odor sensor including the substance absorption film 13 containing nickel particles coated with silica as the fine particles 21 and a silanization agent as the surface modifier (hereinafter, referred to as an "odor sensor B") as the odor sensor 10 according to Embodiment 1, reaction properties with respect to each of water, ammonia, an acetic acid, ethanol, acetone, hexane were checked. Here, the nickel particles coated with silica are fine particles in which nickel particles as the conductive fine particles 27a are covered with a silica film in the fine particles 21 as illustrated in FIG. 2C. The detector 15 of the odor sensor A was a CMOS sensor. As the silanization agent, 1,1,1,3,3,3-hexamethyl disilazane was used.

Figure 8:
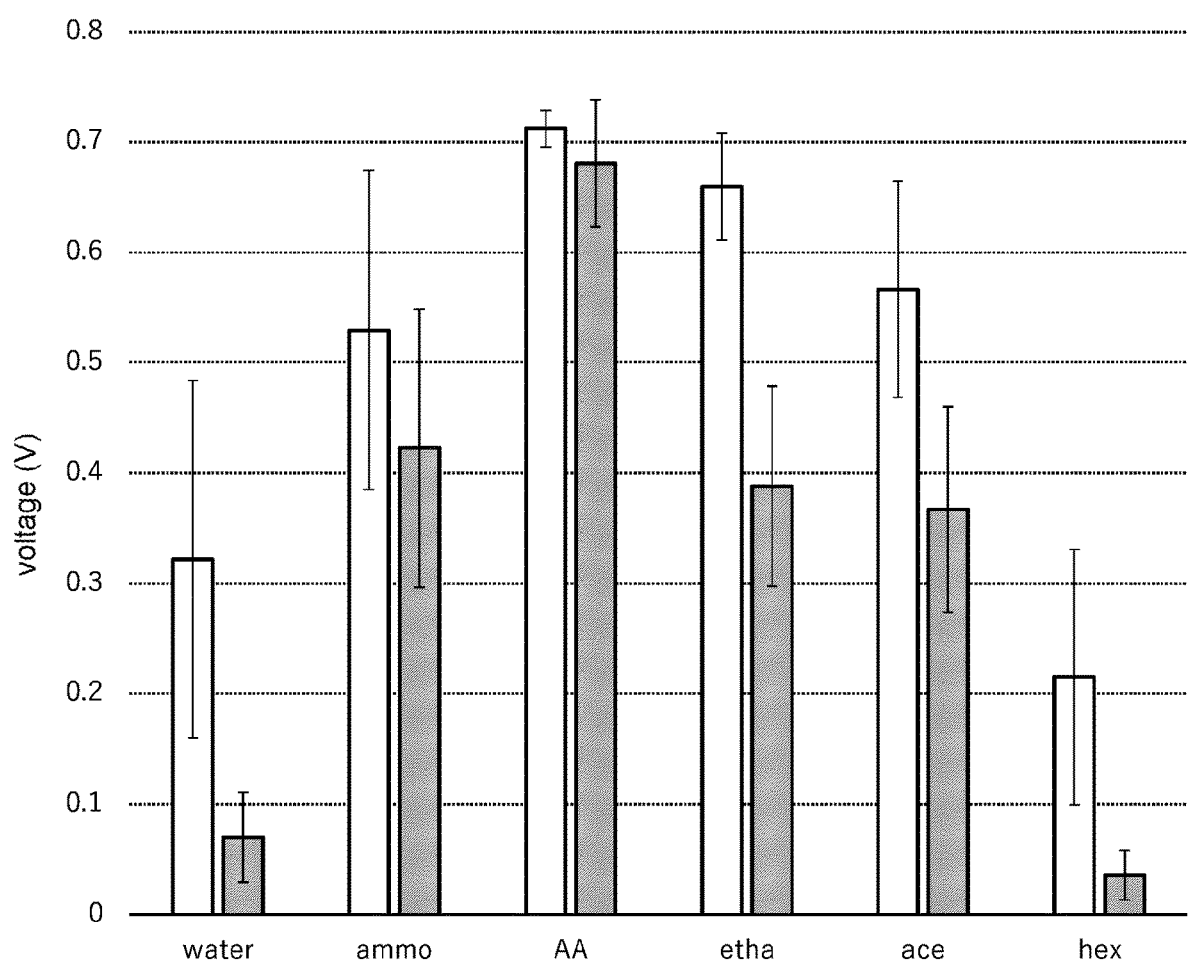
FIG. 8 is a graph illustrating reaction properties of an odor sensor B.

A graph illustrating the reaction properties of the odor sensor B with respect to each of samples of water, ammonia, an acetic acid, ethanol, acetone, and hexane is illustrated in FIG. 8. In FIG. 8, a vertical axis indicates a result (a voltage (V)) to be detected by the CMOS sensor as a reaction when the odor sensor measures each of the samples. Each of bar graphs in FIG. 8 illustrates the result of the odor sensor in a case where the sample is water ("water" in FIG. 8), ammonia ("ammo" in FIG. 8), an acetic acid ("AA" in FIG. 8), ethanol ("etha" in FIG. 8), acetone ("ace" in FIG. 8), and hexane ("hex" in FIG. 8), in order from the left. In each of the samples, the result of the odor sensor in a case where the substance absorption film is a film to which only the nickel particles coated with silica (not containing the surface modifier) are applied (an open bar graph in FIG. 8), and a film to which a mixture of the nickel particles coated with silica and an octanoic acid is applied (a hatched bar graph in FIG. 8) is illustrated.

In FIG. 8, the hatched bar graph is the result of the odor sensor B. From FIG. 8, it is found that the odor sensor B including the substance absorption film 13 containing the nickel particles coated with silica of which the surfaces are modified with the silanization agent exhibits a significant difference only with respect to a specific sample such as ethanol "etha", compared to a case where the surfaces are not modified (the open bar graph), and identification properties with respect to the type of odor are imparted to the odor sensor B.

Preferred embodiments of the present invention have been described, but the present invention is not limited thereto, and various modification and changes can be made in the scope of the gist. For example, the present invention includes the following points.

(Point 1) A purpose of an odor sensor is to include a plurality of sensor elements, the sensor element including: a substance absorption film adsorbing an odor substance; and a detection unit detecting adsorption of the odor substance with respect to the substance absorption film, in which the substance absorption film is a porous fine particle film that contains fine particles containing a compound having silicon and oxygen as a skeleton, and a surface modifier for modifying surfaces of the fine particles, and in at least a part of the plurality of sensor elements, compositions of the fine particles and/or the surface modifier are different from each other.

Accordingly, it is possible to provide an odor sensor capable of using an additive that was not capable of being adopted in an odor sensor including a polymer film.

(Point 2) In the odor sensor, the fine particles may have a microporous structure and/or a hollow structure.

(Point 3) In the odor sensor, the fine particles may contain conductive fine particles, or when the fine particles have the hollow structure, the conductive fine particles may be included in a hollow portion.

(Point 4) In the odor sensor, the surface modifier may contain at least one type selected from the group consisting of an inorganic acid, an organic acid, an inorganic salt, an organic salt, and an ionic liquid.

(Point 5) In the odor sensor, the detection unit may be a detector detecting a phenomenon associated with a weight change of the substance absorption film due to the adsorption of the odor substance.

(Point 6) In the odor sensor, the plurality of sensor elements may be arranged on a substrate at a predetermined interval.

(Point 7) In the odor sensor, the detector may be a quartz crystal microbalance (QCM) sensor, and a weight of the substance absorption film may be 2% or less of a weight of a crystal oscillator of the quartz crystal microbalance (QCM) sensor.

(Point 8) In the odor sensor, the detection unit may be a detector detecting a conductivity change of the substance absorption film due to the adsorption of the odor substance.

(Point 9) In the odor sensor, the surface modifier may be a compound reacting with a conductive polymer to decrease conductivity of the conductive polymer.

(Point 10) In the odor sensor, the plurality of sensor elements may be arranged such that the detection units are adjacent to each other, and each of the substance absorption films may be shared in a plurality of adjacent detection units of the plurality of sensor elements adjacent to each other and may cover the plurality of adjacent detection units.

(Point 11) A purpose of an odor measurement system is to include: the odor sensor according to any of the embodiments described herein, the odor sensor detecting an odor of an odor sample; and a data processing unit generating odor data in which each of electrical signals to be acquired from each of a plurality of sensor elements of the odor sensor and information of the odor sample are associated with each other.

(Point 12) A purpose of a method for producing an odor sensor including a plurality of sensor elements, the sensor element including: a substance absorption film adsorbing an odor substance; and a detection unit detecting adsorption of the odor substance with respect to the substance absorption film, is to include: a film disposing step of disposing a porous fine particle film that contains fine particles containing a compound having silicon and oxygen as a skeleton on detection surfaces of a plurality of detection units arranged adjacent to each other and covers the plurality of adjacent detection units; and a surface modifying step of applying a surface modifier for modifying surfaces of the fine particles onto a surface of the fine particle film, the surface modifiers with different compositions being applied for each predetermined region of the surface of the fine particle film.

REFERENCE SIGNS LIST

1: odor measurement system
10, 100, 200: odor sensor
11, 201: sensor element
13, 113, 203: substance absorption film
15, 115: detector
17: sensor substrate
21: fine particles
23: pores
25: micropores
27: conductive fine particles
51: central processing unit
53: storage unit
55: communication unit
60: odor data server
70: sensor arrangement information server
119a, 119b: predetermined region
121: ink jet head
123: ink jet nozzle
205: odor sensor arrangement
207: section
208: small fraction

The invention claimed is:

1. An odor sensor comprising:
a plurality of sensor elements comprising:
  a substance absorption film configured to adsorb an odor substance; and
  a plurality of detection units configured to detect adsorption of the odor substance with respect to the substance absorption film,
wherein the substance absorption film is a porous particle film that contains particles containing a compound having silicon and oxygen as a skeleton, and a surface modifier for modifying surfaces of the particles,
wherein the plurality of sensor elements are arranged such that the plurality of detection units are adjacent to each other, and
wherein the substance absorption film covers the plurality of adjacent detection units.

2. The odor sensor according to claim 1,
wherein the particles have a microporous structure.

3. The odor sensor according to claim 1,
wherein the surface modifier contains at least one type selected from the group consisting of an inorganic acid, an organic acid, an inorganic salt, an organic salt, and an ionic liquid.

4. The odor sensor according to claim 1,
wherein the detection unit is a detector detecting a phenomenon associated with a weight change of the substance absorption film due to the adsorption of the odor substance.

5. The odor sensor according to claim 4,
wherein the detector is a quartz crystal microbalance (QCM) sensor, and
a weight of the substance absorption film is 2% or less of a weight of a crystal oscillator of the quartz crystal microbalance (QCM) sensor.

6. The odor sensor according to claim 1,
wherein the plurality of sensor elements are arranged on a substrate at a predetermined interval.

7. The odor sensor according to claim 1,
wherein the detection unit is a detector detecting a conductivity change of the substance absorption film due to the adsorption of the odor substance.

8. An odor sensor according to claim 1
wherein the particles have a hollow structure with a hollow portion, and wherein conductive particles are included in the hollow portion.

9. An odor measurement system, comprising:
the odor sensor according to claim 1, the odor sensor detecting an odor of an odor sample; and
a data processing unit generating odor data in which each of electrical signals to be acquired from each of a plurality of sensor elements of the odor sensor and information of the odor sample are associated with each other.

* * * * *